(12) United States Patent
Thomson et al.

(10) Patent No.: US 7,449,334 B2
(45) Date of Patent: Nov. 11, 2008

(54) MEDIUM CONTAINING PIPECHOLIC ACID AND GAMMA AMINO BUTYRIC ACID AND CULTURE OF EMBRYONIC STEM CELLS

(75) Inventors: James A. Thomson, Madison, WI (US); Tenneille Ludwig, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 130 days.

(21) Appl. No.: 11/221,457

(22) Filed: Sep. 8, 2005

(65) Prior Publication Data

US 2006/0084168 A1 Apr. 20, 2006

Related U.S. Application Data

(60) Provisional application No. 60/608,040, filed on Sep. 8, 2004.

(51) Int. Cl.
*C12N 5/08* (2006.01)
*C12N 5/02* (2006.01)

(52) U.S. Cl. ............................ 435/377; 435/366
(58) Field of Classification Search ............ 435/366, 435/377, 384
See application file for complete search history.

(56) References Cited

U.S. PATENT DOCUMENTS

2006/0014279 A1* 1/2006 Xu et al. ............... 435/366

FOREIGN PATENT DOCUMENTS

WO  WO 2004/055155 A2  7/2004

OTHER PUBLICATIONS

Xu et al. Feeder-Free Growth of Undifferentiated Human Embryonic Stem Cells. Nature Biotechnology. vol. 19, pp. 971-974.*
Miyazono, Kohei, "Positive and negative regulation of TGF-B signaling," Journal of Cell Science 113:1101-1109 (2000).
Reya, T., et al., "A role for Wnt signalling in self-renewal of haematopoietic stem cells," Natur 423:409-414 (2003).
Ying, Q., et al., "BMP Induction of Id Proteins Suppresses Differentiation and Sustains Embryonic Stem Cell Self-Renewal in Collaboration with STAT3," Cell 115:281-292 (2003).
Amit, M., et al., "Feeder Layer- and Serum-Free Culture of Human Embryonic Stem Cells," Biology of Reproduction 70:837-845 (2004).

* cited by examiner

*Primary Examiner*—Deborah Crouch
(74) *Attorney, Agent, or Firm*—Quarles & Brady LLP

(57) ABSTRACT

Previous methods for culturing human embryonic stem cells have required either fibroblast feeder cells or a medium which has been exposed to fibroblast feeder cells in order to maintain the stem cells in an undifferentiated state. It has now been found that if high levels of fibroblast growth factor, gamma amino butyric acid, pipecholic acid, lithium and transforming growth factor beta are added to the medium in which the stem cells are cultured, the stem cells will remain undifferentiated indefinitely through multiple passages, even without feeder cells or conditioned medium.

17 Claims, 4 Drawing Sheets

US 7,449,334 B2

MEDIUM CONTAINING PIPECHOLIC ACID AND GAMMA AMINO BUTYRIC ACID AND CULTURE OF EMBRYONIC STEM CELLS

CROSS-REFERENCE TO RELATED APPLICATIONS

This application claims priority from U.S. provisional patent application Ser. No. 60/608,040 filed Sep. 8, 2004.

STATEMENT REGARDING FEDERALLY SPONSORED RESEARCH OR DEVELOPMENT

This invention was made with United States government support awarded by the following agencies: NIH RR17721. The United States has certain rights in this invention.

BACKGROUND OF THE INVENTION

Stem cells are defined as cells that are capable of differentiation into many other differentiated cell types. Embryonic stem cells are stem cells from embryos which are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated here as human ES cell, which is an embryonic stem cell derived from a human embryonic source. Human embryonic stem cells are of great scientific interest because they are capable of indefinite proliferation in culture and are thus capable, at least in principle, of supplying cells and tissues for replacement of failing or defective human tissue. The existence in culture of human embryonic stem cells offers the potential of unlimited amounts of human cells and tissues for use in a variety of therapeutic protocols to assist in human health. It is envisioned in the future human embryonic stem cells will be proliferated and directed to differentiate into specific lineages so as to develop differentiated cells or tissues which can be transplanted into human bodies for therapeutic purposes. Human embryonic stem cells and the differentiated cells that may be derived from them are also powerful scientific tools for the study of human cellular and developmental systems.

The basic techniques to create and culture human embryonic stem cells have been described. The previously reported techniques do work, but there are limitations and drawbacks to many of the procedures currently used to culture human embryonic stem cells. One limitation is of particular concern. Most existing human embryonic stem cell lines have been, to one degree or another, exposed directly to mouse cells or to a medium in which mouse cells have been cultured previously. The fact that some ES cells from existing cell lines were found to exhibit the sialic residue Neu5Gc, which is not normally made by human cells, received much attention in the press. The original techniques for the generation and culture of human embryonic stem cells required the use of mouse embryonic fibroblast (MEF) feeder cells as a feeder layer on which human embryonic stem cells could be cultured. The fibroblast feeder cells acts, through some as yet incompletely understood mechanism, to encourage the stem cells to remain in an undifferentiated state. Later, it was discovered that the same phenomenon could be achieved if the stem cells were exposed to "conditioned media." Conditioned medium is a stem cell culture medium with which feeder cells, such as MEFs, had been previously been cultured. Either the feeder cells imparted some factor to the medium or removed some factor from the medium, but the result is that conditioned medium can be used to culture stem cells without differentiation. Either culture condition, the direct growth of human ES on murine feeder cells, or the use of conditioned media, raises the concern that one or more agents such as a virus could transmit from the mouse cells to the human ES cells. If one of the objectives of human embryonic stem cell cultures is to create tissues which can ultimately be transplanted into a human body, it is highly desirable that the stem cells never have been exposed to cells of another species or to media which have been used to culture cells of another species. Accordingly, defining a culture condition, which will permit the proliferation and culture of human embryonic stem cells without a fibroblast feeder layer, is of great interest in the continued development of techniques for the long term culture of human embryonic stem cells.

A characteristic trait of human embryonic stem cells in culture is that if conditions are less than ideal, the cells have a tendency to differentiate. It is easy to induce human ES cells to differentiate while it is demanding to maintain the human ES cells in undifferentiated state in culture. Most culture conditions will results in some level of unwanted differentiation, particularly around the periphery of the growing ES cell colony. While ES cells can be cultured with some degree of unwanted differentiation, the objective is to define a culture condition that permits the culture to remain as undifferentiated as possible, i.e. with as few differentiated cells as possible. We believe that we have used particularly stringent standards to define conditions that will support the indefinite culture of undifferentiated ES cell cultures.

Several medium formulations will permit human ES cells to remain undifferentiated for some time, but that state often fails to maintain itself. In particular, we define the growth of human ES cells from an initial seed culture in a culture vessel to confluence in the same culture vessel as a "passage." We have found several medium formulations that permit the cultivation of human ES cells for one or two passages without severe differentiation, but then the cells differentiate rapidly upon subsequent passages. We have come to believe that in order for a medium to truly support the indefinite proliferation of human ES cells without differentiation, without conditioned medium or fibroblast feeder cells, the medium must be demonstrated to support culture of human ES cells in a substantially uniform and undifferentiated state for at least five passages. It is also important that the cultures remain relatively homogenous and undifferentiated throughout the culture period and retain all of the important characteristics of human ES cells.

The state of differentiation of a stem cell culture can be assessed most easily by judging the morphological characteristics of the cells. Undifferentiated stem cells have a characteristic morphology, i.e. small and compact cells with clearly defined cell borders, a morphology which can be easily seen by examination of a stem cell culture under a microscope. By contrast, cells which have differentiated appear larger and more diffuse, with indistinct borders. While some differentiated cells can, and normally do, appear at the margin of colonies of undifferentiated cells, the optimal stem cell culture is one that proliferates in the culture vessel with only minimal numbers of cells at the periphery of the culture appearing to be differentiated. With experience, one can judge the status of differentiation and health of human ES cell cultures visually with good accuracy. A biochemical marker that is used to track the status of ES cells as undifferentiated is the presence of the transcription factor Oct4, which has come to be regarded as the most reliable marker of undifferentiated status of ES cells, and which is one of the first markers lost as undifferentiated cells begin to differentiate.

BRIEF SUMMARY OF THE INVENTION

The present invention is summarized as a method for culturing human embryonic stem cells without the need for feeder cells or conditioned medium, the method including the step of culturing the human embryonic stem cells in a medium including salts, vitamins, amino acids, glucose, a fibroblast growth factor, gamma amino butyric acid, pipecholic acid, lithium and transforming growth factor beta, all in sufficient amount to maintain the stem cells in an undifferentiated state through multiple culture passages.

The present invention is also directed to an in vitro cell culture of human embryonic stem cells cultured in a medium including high levels of a fibroblast growth factor, gamma amino butyric acid, pipecholic acid, lithium and transforming growth factor beta so that the stem cells can be cultured indefinitely in an undifferentiated state without the need for fibroblast feeder cells or conditioned medium.

It is an object of the present invention to define long term culture conditions for human embryonic stem cells that avoid the use of or exposure to animal cells and animal proteins, whether from feeder cells or for conditioning medium in which stem cells are cultured.

It is another object of the present invention to define culture conditions for human embryonic stem cells that are as defined as possible while maintaining the maximum proportion of cell in the culture as possible in an undifferentiated state.

Other objects, features and advantages of the present invention will become apparent from the following specification.

DETAILED DESCRIPTION OF THE INVENTION

Figure 1:
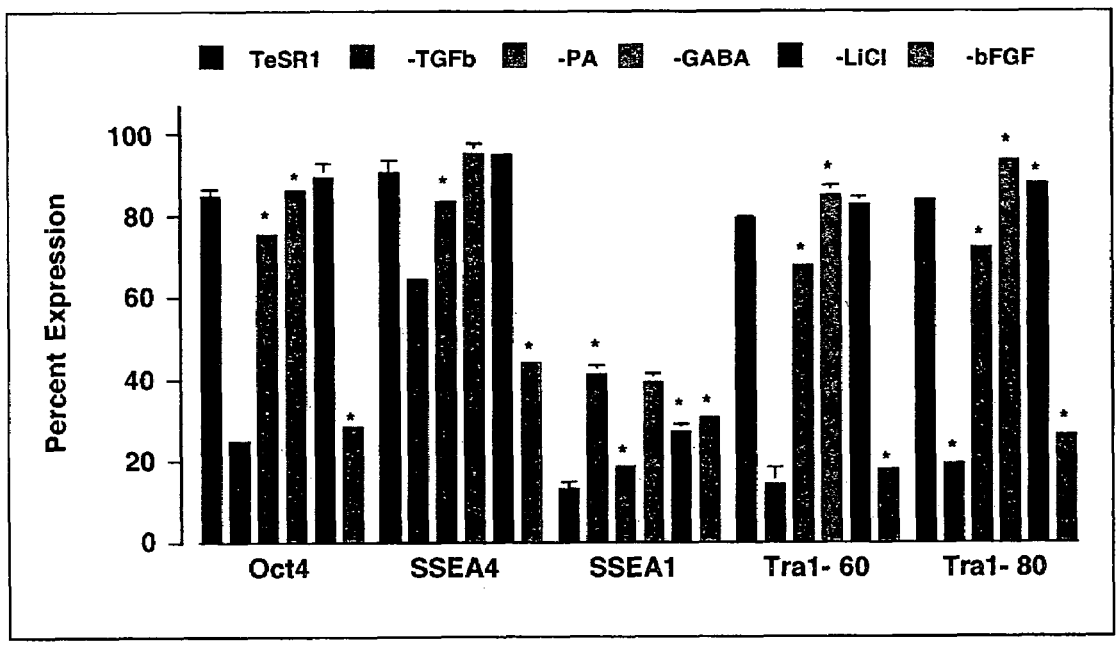
FIG. 1 presents data from experimental work described in the specification below showing that the components of the medium reduce the proportion of differentiated cells in the culture of human ES cells grown in it.

We have identified multiple culture conditions and media which permit the indefinite culture and robust proliferation of human embryonic stem cells in an undifferentiated state and also in the absence of both feeder cells and conditioned medium. The development of these media and culture conditions make possible the derivation and maintenance of human ES cell lines in defined and controlled conditions without direct or indirect exposure to animal cells of any kind. These media have been demonstrated to support undifferentiated ES cell proliferation through multiple passages, at least five, which is firm evidence that these media will support such cultures indefinitely.

A defined and humanized medium for the culture and proliferation of human ES cells typically includes salts, vitamins, a source of glucose, minerals and amino acids. To supplement the medium and supply conditions to support cell growth, initially stem cell media included serum from one source or another. Also previously, it has been reported that the addition of fibroblast growth factor plus a serum replacement additive will permit the cultivation of human ES cells without serum. The serum replacement can be a commercially available product sold for that purpose or can be a formulated mixture of protein, such as serum albumin, vitamins, salts, minerals, a transferrin or transferrin substitute, and insulin or an insulin substitute. This serum replacement component may also be supplemented with selenium. It is preferred here that a defined serum replacement be used in lieu of serum from any source in culturing human ES cells, in order to avoid the issues of variation in serum constituents and to use media that are as defined as possible. We have defined a sufficient medium, and all of the components of the medium taught here are disclosed in Table 1 set forth below, which lists all the components of our medium, designated TeSR1, by concentration of the constituents. The TeSR1 medium is comprised of a DMEM/DF12 base, supplemented with human serum albumin, vitamins, antioxidants, trace minerals, specific lipids, and cloned growth factors.

To avoid the need for a fibroblast feeder layer, previously thought to be necessary to maintain human ES cells in an undifferentiated state, it is reported here that the combination of the use of higher concentrations of FGF (10 to 1000 ng/ml) together with the use of GABA (gamma aminobutyric acid), pipecholic acid (PA), lithium (LiCl) and transforming growth factor beta (TGFβ), will enable a medium to support undifferentiated stem cell growth. The combination of these additives has been found to be sufficient to maintain the culture of human ES cells in an undifferentiated state indefinitely without exposure to either feeder cells or conditioned media. These additives are demonstrably sufficient. However, all of them may not be necessary for every medium formulation. By selective deletion of these additives, one or more of these components can be deleted resulting in human ES cell cultures that will still grow at a loss of purity of undifferentiated status in the cultures. Such cultures may or may not remain stable over many passages. However, it is clear that the combination is sufficient to enable a variety of media that will support the long term culture and proliferation of undifferentiated human ES cells through an indefinite number of passages without feeder cells or conditioned medium.

Figure 4:
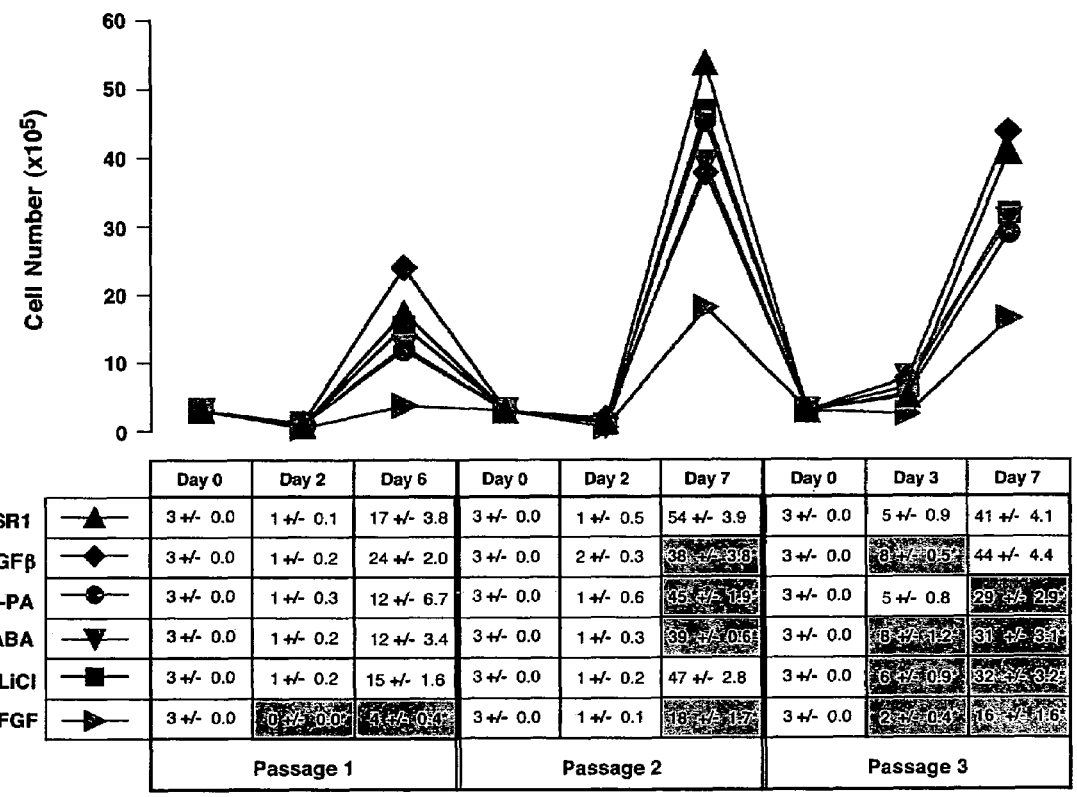
FIG. 4 is a graphical representation of data showing that the medium described here results in robust growth of stem cell cultures.

Our initial subjective screens of these individual growth factors, chosen because of the receptors expressed by human ES cells, identified several factors as having positive effects on undifferentiated proliferation. Of these, bFGF, LiCl, γ-aminobutyric acid (GABA), pipecholic acid, and TGFβ were ultimately included in TeSR1. For each of the four cell lines tested, the proliferation rate and the percentage of cells maintaining expression of characteristic human ES cell markers were higher in TeSR1 than in control cells cultured in fibroblast-conditioned medium, and removal of any one of these five factors decreased culture performance. Some of these data are illustrated in FIG. 1, which shows that cultures grown in media with any one of these constituents omitted exhibited a lesser percentage of cells which remained undifferentiated as compared to cultures with all four of these medium constituents included. Note that Oct4, SSEA-1, SSEA-4, Tral-60 and Tral-80 are all cell surface markers or transcription factors (Oct4) which are used to track the differentiation status of stem cells. FIG. 4 illustrates similar trials in which it was demonstrated that over multiple passages the growth rate of the cultures was the highest when all these constituents together were in the culture medium.

It is also helpful to include in the culture conditions for the human ES cells a biological matrix in the culture vessel. One such material that has been used is Matrigel™, which is an artificial basement membrane of mouse cell origin, which is supplied as a commercial product free of mouse cells. Another material of human origin also known now to serve a similar purpose is fibronectin, a human glycoprotein which is used in its insoluble form to create a fiber matrix also to serve as a basement membrane for ES cell culture. In our hands a matrix of fibronectin alone was not sufficient. However, it has also now been found that a human matrix material can be made of a combination of the human matrix proteins collagen IV, fibronectin, laminin, and vitronectin and this matrix suffices to support human ES cells indefinitely in an undifferentiated state in the TeSR1 medium.

Arriving at the above listed medium additives followed the methodical testing of over 80 individual growth factors. While some of the additives seemed, at least for a few passages, to support in the growth of human ES cells in culture, many failed in subsequent passages to maintain the ES cells in an undifferentiated state. We were did not identify other combinations of these factors which gave the results of the media additives described in the examples below. This is not to say the constituents are not subject to some variation. For example, the LiCl is used in the medium because it stimulates the wnt pathway. Wnts themselves or other stimulators of this pathway such as activin could be substituted as equivalents to LiCl, even though LiCl is the likely the most economical agent for this purpose. Similarly, the GABA is believed to interact with the GABA receptor, and the scientific literature includes the identification of several molecules which are agonists of that same receptor and might be substituted for GABA in the medium as an equivalent. It is also believed that PA also interacts with the GABA receptor. While both PA and GABA were found to be helpful in the medium at the concentrations used here, it is also envisioned that one or the other of these constituents could be dramatically increased in concentration to obviate the need for the other.

The fibroblast growth factor in higher concentrations (40 to 100 ng/ml) seems to obviated the need for feeder cells. The preferred FGF is basic FGF, also referred to as bFGF and FGF2, but other FGFs including at least FGF4, FGF9, FGF17 and FGF18 will suffice for this purpose as well. Other FGFs may also work, even if at higher concentrations.

The observation that human embryonic stem (ES) cell cultures have previously been maintained in an undifferentiated state only when cultured in the presence of fibroblast feeder cells or in conditioned medium has led to speculation that the fibroblasts release into the medium a factor which acts to inhibit differentiation of the ES cells. However, whatever effect that is mediated by the fibroblast feeder cells to the medium, it is now clear that the medium described below will substitute for that effect. The three media defined below are defined, contain no animal cells, and permit the long term culture of undifferentiated human ES cells in an undifferentiated state. An example is also presented of a medium in which the proteins in the medium are all human, to have a "humanized" medium and culture conditions to avoid any possible concerns about sub-cellular products of animal origin.

EXAMPLES

The constituents of TeSR1 medium, which was used for all cultures described here unless otherwise indicated, is set forth in Table 1 below. Our preliminary experiments suggested that undifferentiated human ES cell proliferation was optimal at a pH of 7.2, an osmolarity of 350 mOsMol, and an atmosphere of 10% $CO_2$/5% $O_2$. These conditions were used for all subsequent cultures described here.

Cells of human ES lines H1, H7, H9, and H14 cells have all proliferated robustly in TeSR1 for 11, 7, 25, and 17 passages respectively (2-6 months). The karyotypes were confirmed normal for cell line H14 after 7 passages, and H9 after 8 and 21 passages. Teratoma formation was confirmed for H1 and H9 after 11 and 20 passages.

Figure 2:
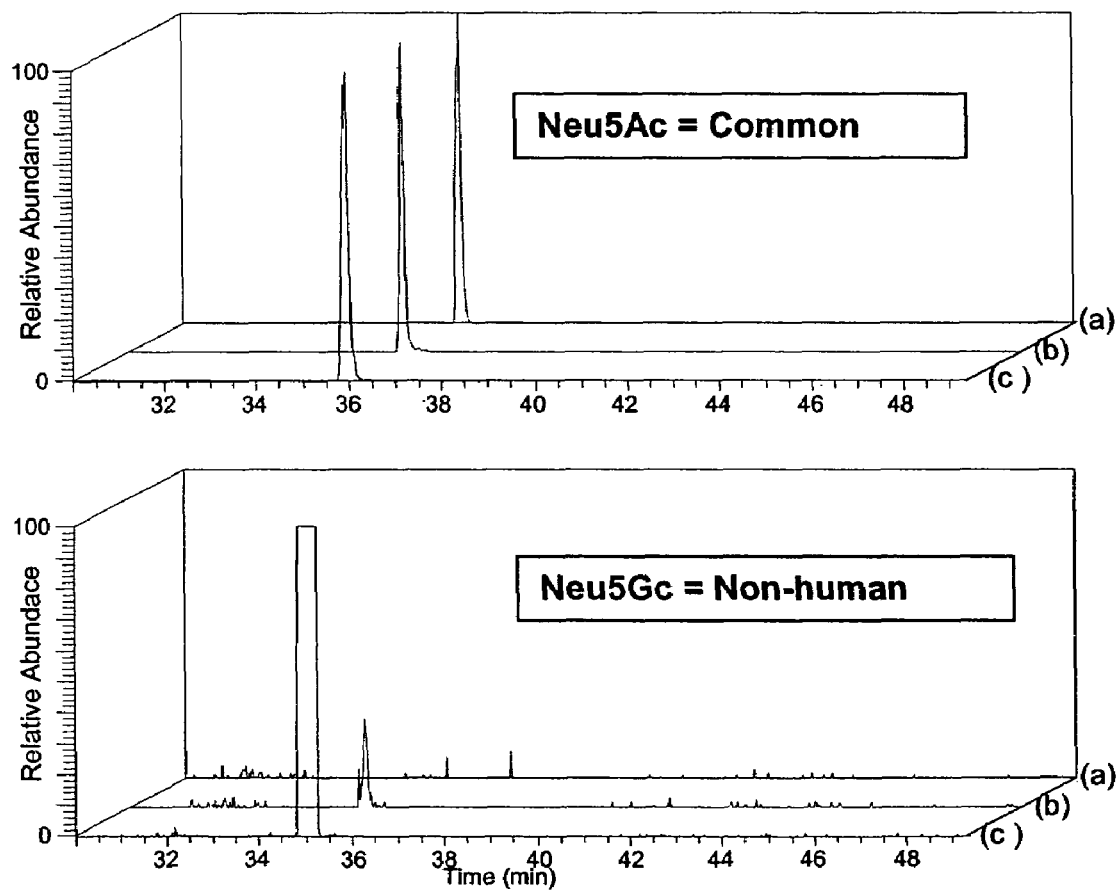
FIG. 2 presents a graphical presentation of data showing that the medium with human matrix proteins results in cultured human ES cells which do not exhibit a sialic acid residue of non-human origin.

It has been suggested that prior ES cell cultures are less than optimal because of the presence of Neu5Gc, a sialic acid not made by humans. Because the human matrix components collagen, fibronectin, laminin and vitronectin eliminated the final animal product from the TeSR1 culture conditions for human ES cells, we tested whether Neu5Gc was eliminated from existing human ES cell lines during culture in this medium. We confirmed the presence of Neu5Gc on human ES cells cultured in fibroblast conditioned medium, detected a reduced but detectable amount on cells cultured in TeSR1 on Matrigel, and could not detect any Neu5Gc on ES cells cultured in TeSR1 using the four human matrix components. These data are illustrated in FIG. 2. Thus human ES cells cultured on TeSR1 and on a matrix of human proteins do not exhibit the non-human sialic acid residues found in cells cultured on murine feeder cells.

Figure 3:
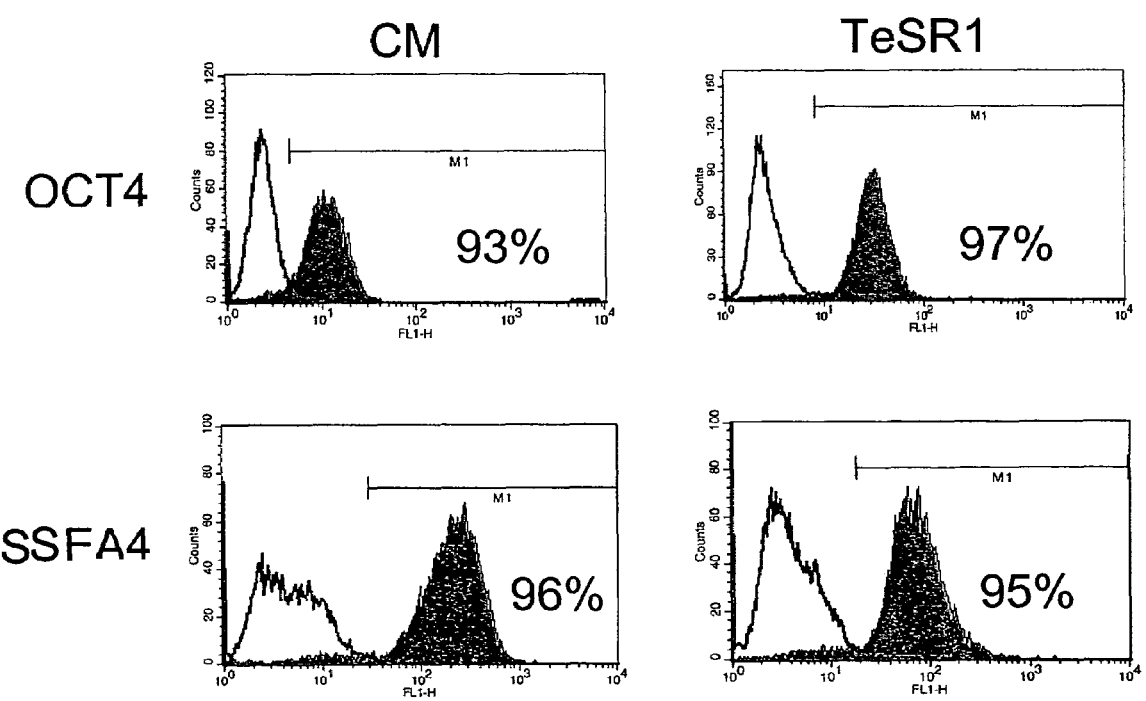
FIG. 3 is a graphical presentation of data showing the high level of undifferentiated cells in the human stem cell culture.

To test the conditions of the ES cell colonies and the suitability of the culture for the long term maintenance of human ES cell cultures, the TeSR1 medium was compared to the best prior medium condition, which in ours hands is the use of conditioned medium. It was found that the TeSR1 medium was capable of maintaining the human ES cells in such an undifferentiated state that over 90% of the cells continued to test positive for Oct 4 even after long term culture. The results of this test are presented in the graph of FIG. 3. This represents the first instance known in which any feeder free and conditioned medium free medium has maintained a level of undifferentiated growth of human ES cells to the extent that over 90% of the cells in the culture remain undifferentiated at all stages.

The growth curve and FACS analysis of H1 cells cultured for 3 passages was measured in TeSR1 medium and in TeSR medium from which each the following components had been omitted: TGFβ, PA, LiCl, GABA and bFGF. To start the cultures, $3 \times 10^5$ cells from each cell line were plated on Day 0 of passage 1. Cell numbers were counted from triplicate wells to assess attachment (day 2-3) and final cell number at passage (day 6-7). Initial plating density and sampling times were repeated, when possible, for 5 passages. Cells were analyzed on day 6 of passage 3 by FACS for cell surface markers SSEA1, SSEA4, Tra 1-60 and Tra 1-81 and for the transcription factor Oct4. This data is presented graphically in FIG. 1. These data show that human ES cells can be cultured in media lacking each of these components at the cost of some unwanted differentiation of cells in the culture, and that the highest level of undifferentiated culture could only be achieved by using all of these components. Similar results were obtained with other cells lines as well.

The pluripotency of human ES cell lines maintained in TeSR1 medium was tested. Cells of newly initiated cell lines WA01 and WA09, cultured in TeSR1 Medium on Matrigel matrix for 11 and 20 passages, respectively were injected into SCID-beige mice. Teratomas exhibiting complex differentiation developed in the mice 6-8 weeks post-inoculation.

TABLE 1

Complete Formulation for TeSR1 Medium

| | mM |
|---|---|
| INORGANIC SALTS | |
| Calcium chloride (Anhydrous) | 0.8232 |
| HEPES | 11.76 |
| Magnesium chloride (Anhydrous) | 0.2352 |
| Magnesium Sulfate (MgSO4) | 0.319088 |
| Potassium chloride (KCl) | 3.26144 |
| Sodium bicarbonate (NaHCO3) | 11.2112 |
| Sodium chloride (NaCl) | 94.55824 |
| Sodium phosphate, dibas (Anhydrous) | 0.392 |
| Sodium phosphate, mono. (NaH2PO4-H20) | 0.355152 |
| TRACE MINERALS | |
| Ferric Nitrate (Fe(NO3)3-9H2O) | 0.00009408 |
| Ferric sulfate (FeSO4-7H2O) | 0.001176 |
| Cupric sulfate (CuSO4-5H2O) | 4.0768E−06 |
| Zinc sulfate (ZnSO4-7H2O) | 0.001176 |
| Ammonium Metavanadate NH4VO3 | 0.000056 |
| Mangenous Sulfate Mn SO4 H2O | 1.00592E−05 |
| Ammonium Molybdate | 1.00404E−05 |
| NiSO4 6H2O | 4.94861E−06 |
| Sodium Meta Silicate Na2SiO3 9H2O | 0.004926108 |
| SnCl2 | 5.32544E−06 |
| CdCl2 | 6.21931E−05 |
| CrCl3 | 9.41176E−06 |
| AgNo3 | 5.00293E−06 |
| AlCl3 6H2O | 2.4855E−05 |
| Ba (C2H3O2)2 | 4.99217E−05 |
| CoCl2 6H2O | 5.0021E−05 |
| GeO2 | 2.5337E−05 |
| KBr | 5.04202E−06 |
| KI | 5.12048E−06 |
| NaF | 0.000500119 |
| RbCl | 5.00414E−05 |
| ZrOCl2 8H2O | 9.03834E−05 |
| GROWTH FACTORS | |
| GABA | 0.979 |
| Pipecholic Acid | 0.000984 |
| bFGF | 5.80E−06 |
| LiCl | 0.979 |
| TGF beta 1 | 2.35E−08 |
| LIPIDS | |
| Linoleic Acid | 0.0070976 |
| Lipoic Acid | 0.00039984 |
| Arachidonic Acid | 0.001312 |
| Cholesterol | 0.0113798 |
| DL-alpha tocopherol-acetate | 0.02962 |
| Linolenic Acid | 0.007184 |
| Myristic Acid | 0.008758 |
| Oleic Acid | 0.00708 |
| Palmitoleic Acid | 0.007862 |
| Stearic Acid | 0.00703 |
| AMINO ACIDS | |
| L-Alanine | 0.1392 |
| L-Arginine hydrochloride | 0.5488 |
| L-Asparagine-H2O | 0.1392 |
| L-Aspartic acid | 0.1392 |
| L-Cysteine-HCl-H2O | 0.0784 |
| L-Cystine 2HCl | 0.0784 |
| L-Glutamic acid | 0.1392 |
| L-Glutamine | 2.96 |
| Glycine | 0.296 |
| L-Histidine-HCl-H2O | 0.1176 |
| L-Isoleucine | 0.326144 |
| L-Leucine | 0.353584 |
| L-Lysine hydrochloride | 0.391216 |
| L-Methionine | 0.090944 |
| L-Phenylalanine | 0.16856 |
| L-Proline | 0.2176 |
| L-Serine | 0.296 |
| L-Threonine | 0.352016 |
| L-Tryptophan | 0.0346528 |
| L-Tyrosine 2Na 2H2O | 0.167776 |
| L-Valine | 0.354368 |
| VITAMINS | |
| Ascorbic acid | 0.375 |
| Biotin | 1.12112E−05 |
| Choline chloride | 0.0502544 |
| D-Calcium pantothenate | 0.0036064 |
| Folic acid | 0.004704 |
| i-Inositol | 0.05488 |
| Niacinamide | 0.012936 |
| Pyridoxine hydrochloride | 0.0076048 |
| Riboflavin | 0.0004704 |
| Thiamine hydrochloride | 0.02460217 |
| Vitamin B12 | 0.000392 |
| ENERGY SUBSTRATES | |
| D-Glucose | 13.72784 |
| Sodium Pyruvate | 0.392 |
| PROTEINS | |
| Human Insulin | 0.0034438 |
| Human Holo-Transferrin | 0.14 |
| Human Serum Albumin | 199.7 |
| OTHER COMPONENTS | |
| Glutathione (reduced) | 0.00592996 |
| Hypoxanthine Na | 0.01176 |
| Phenol red | 0.0159936 |
| Putrescine-2HCl | 0.000394352 |
| Thymidine | 0.001176 |
| 2-mercaptoethanol | 0.1 |
| Selenium | 0.000177304 |
| Pluronic F-68 | 0.238 |
| Tween 80 | 0.3358 |

We claim:

1. A method for culturing human stem cells in an undifferentiated state on a matrix without the need for feeder cells or conditioned medium, the method comprising the step of:
culturing human embryonic stem cells on a matrix that comprises a solubulized basement membrane preparation extracted from the Engelbreth-Holm-Swarm mouse sarcoma or a matrix that comprises human matrix proteins collagen IV, fibronectin, laminin, and vitronectin in a medium absent feeder cells and conditioned media, the medium comprising salts, vitamins, amino acids, glucose, a fibroblast growth factor, gamma amino butyric acid, pipecholic acid, lithium and transforming growth factor beta, in sufficient amounts to maintain the human stem cells in an undifferentiated state through multiple successive culture passages.

2. The method of claim 1 wherein the medium includes the fibroblast growth factor in a concentration of at least 40 ng/ml.

3. The method of claim 1 wherein the medium also comprises a transferrin or a transferrin substitute and insulin or an insulin substitute.

4. In a method of culturing human embryonic stem cells on a matrix that comprises a solubulized basement membrane preparation extracted from the Engeibreth-Hoim-Swarm mouse sarcoma or a matrix that comprises human matrix proteins collagen IV, fibronectin, laminin, and vitronectin and in a medium including salts, vitamins, amino acids, and a fibroblast growth factor, the improvement comprising adding to the medium an amount of gamma amino butyric acid, pipecholic acid, lithium and transforming growth factor beta in an amount sufficient to maintain the cells in an undifferentiated state through multiple successive culture passages.

5. An in vitro cell culture comprising in a culture vessel:
human embryonic stem cells;
a matrix on which stem cells can grow, wherein the matrix comprises a solubulized basement membrane preparation extracted from the Engelbreth-Holm-Swarm mouse sarcoma or the human matrix proteins collagen IV, fibronectin, laminin, and vitronectin; and
a culture medium, the culture medium comprising salts, vitamins, amino acids, glucose, a fibroblast growth factor, gamma amino butyric acid, pipecholic acid, lithium and transforming growth factor beta in sufficient amounts to maintain the human stem cells in an undifferentiated state through multiple culture passages, the medium being free of feeder cells and never having been exposed to feeder cells.

6. A cell culture as claimed in claim 5 wherein the medium comprises the fibroblast growth factor in a concentration of at least 40 ng/ml.

7. A cell culture as claimed in claim 5 wherein the medium comprises the fibroblast growth factor in a concentration of at least 100 ng/ml.

8. A cell culture as claimed in claim 5 wherein the medium further comprises proteins selected from albumin, insulin or an insulin substitute and a transferrin or a transferrin substitute.

9. A cell culture as claimed in claim 8 wherein the insulin and transferrin are recombinant proteins.

10. A culture of human embryonic stem cells comprising undifferentiated human stem cells, a matrix that comprises the human matrix proteins collagen IV, fibronectin, laminin, and vitronectin, and a culture medium, the culture free of feeder cells and medium exposed to feeder cells, the medium also free of products from non-human animals, the human embryonic stem cells proliferating in an undifferentiated state and being at least 90% positive for the transcription factor Oct4 through prolonged culture.

11. A culture of human embryonic stem cells as claimed in claim 10 wherein the cells do not exhibit the sialic acid residue Neu5Gc.

12. A medium for culturing stem cells, the medium comprising salts, vitamins, amino acids, glucose, a fibroblast growth factor, gamma amino butyric acid, pipecholic acid, lithium and transforming growth factor beta in sufficient amounts to maintain stem cells grown in the medium in an undifferentiated state through multiple culture passages.

13. The medium of claim 12, wherein the medium further comprises proteins selected from albumin, insulin and transferrin.

14. The method of claim 1, wherein the matrix comprises human matrix proteins collagen IV, fibronectin, laminin, and vitronectin.

15. The method of claim 4, wherein the matrix comprises human matrix proteins collagen IV, fibronectin, laminin, and vitronectin.

16. The in vitro cell culture of claim 5, wherein the matrix comprises human matrix proteins collagen IV, fibronectin, laminin, and vitronectin.

17. The medium of claim 12, wherein the medium is free of products from non-human animals.

* * * * *